United States Patent

(12) United States Patent
Ogawa et al.

(10) Patent No.: US 8,247,350 B2
(45) Date of Patent: Aug. 21, 2012

(54) ADJUVANT COMPOSITION, AGROCHEMICAL SPRAY AQUEOUS SOLUTION CONTAINING THE SAME AND CONTROL METHOD USING THE SAME

(75) Inventors: Kazuteru Ogawa, Kamisu (JP); Yasuhito Kato, Kamisu (JP); Sumihiko Miyahara, Saitama (JP); Eiji Makino, Saitama (JP); Yoshihiko Usui, Saitama (JP)

(73) Assignees: National Agriculture And Food Research Organization, Ibaraki (JP); Nippon Kayaku Kabushiki Kaisha, Tokyo (JP)

( * ) Notice: Subject to any disclaimer, the term of this patent is extended or adjusted under 35 U.S.C. 154(b) by 481 days.

(21) Appl. No.: 12/449,704

(22) PCT Filed: Mar. 6, 2008

(86) PCT No.: PCT/JP2008/054046
§ 371 (c)(1),
(2), (4) Date: Aug. 21, 2009

(87) PCT Pub. No.: WO2008/111482
PCT Pub. Date: Sep. 18, 2008

(65) Prior Publication Data
US 2010/0099569 A1    Apr. 22, 2010

(30) Foreign Application Priority Data
Mar. 9, 2007 (JP) ................................. 2007-059552

(51) Int. Cl.
*A01N 25/00* (2006.01)
(52) U.S. Cl. .................................................. 504/116.1
(58) Field of Classification Search ........................ None
See application file for complete search history.

(56) References Cited

FOREIGN PATENT DOCUMENTS

| | | |
|---|---|---|
| CN | 1406481 | 4/2003 |
| EP | 1023835 * | 8/2000 |
| JP | 7-196608 | 8/1995 |
| JP | 11-228312 | 8/1999 |
| JP | 2001-151613 | 6/2001 |
| JP | 2004-083540 | 3/2004 |
| JP | 2006-248994 | 9/2006 |
| WO | 2005002336 * | 7/2004 |

OTHER PUBLICATIONS

International Search Report dated Jun. 10, 2008.
Edited by Pesticide Science Society of Japan, Noyaku Seizai, Shiyoho Kenkyukai, Noyaku Seizai, Guide, Japan Plant Protection Association, Oct. 30, 1997, pp. 100 to 112.
Edited by Kagaku Daijiten Henshu Iinkai, Kagaku Daijiten 6, reduced-size edition, $32^{nd}$ print, Kyoritsu Shuppan Co., Ltd., Aug. 15, 1989, p. 277.
Kozo Tsuji, "Noyaku Seizai Hayawakari—Seizai de Konnakoto ga Dekiru—", first edition, first print, The Chemical Daily Co., Ltd., Oct. 24, 2006, pp. 143 to 158.
Edited by Tokiyuki Yoshida, New Edition Kaimen Kasseizai Handbook, forth edition, Kogaku Tosho Kabushiki Kaisha, May 20, 2000, pp. 116 to 127.

* cited by examiner

*Primary Examiner* — Alton Pryor
(74) *Attorney, Agent, or Firm* — Nields, Lemack & Frame, LLC

(57) ABSTRACT

The present invention relates to an adjuvant composition characterized by containing the following (A) and (B):
(A) Sodium dialkylsulfosuccinate and polyoxyethylene alkyl ether, the total content being 45% to 85% by mass;
(B) 5 to 40% by mass of component for pour-point depressant,
and the adjuvant composition can uniformly adhere agrochemical active ingredients to crops, has an effect to stabilize the agrochemical efficacy and particularly exerts a pronounced effect when used in drift-reducing spraying.

**18 Claims, No

ADJUVANT COMPOSITION, AGROCHEMICAL SPRAY AQUEOUS SOLUTION CONTAINING THE SAME AND CONTROL METHOD USING THE SAME

TECHNICAL FIELD

The present invention relates to an adjuvant composition for uniformly adhering agrochemical active ingredients to crops while reducing drift when spraying agrochemicals, an agrochemical spray aqueous solution to which the adjuvant composition is added, and a method for spraying the agrochemical spray aqueous solution.

BACKGROUND ART

Many cases are known where an anionic surfactant susceptible to cationic active ingredients and to agrochemical formulation compositions and a nonionic surfactant susceptible to changes in temperature are used in combination as spreading agents in order to overcome the drawbacks of the both. For example, Non-Patent Literature 1 describes trade names such as Gramin S (which is a trade name, manufactured by Sankyo Agro Co., Ltd.: 5% polyoxyethylene fatty acid ester, 15% polyoxyethylene nonylphenyl ether and 4% sodium polynaphthylmethanesulfonate), Tokuace (which is a trade name, manufactured by Sankyo Agro Co., Ltd.: 9% sodium dialkylsulfosuccinate and 31% polyoxyethylene alkylphenyl ether) and RABIDEN 3S (which is a trade name: 1.4% sodium dioctylsulfosuccinate, 8% polyoxyethylene alkyl ether, 3% polyoxyethylene fatty acid ester). These are commercially available and the dilution factor when used is from 3,000-fold to 10,000-fold. By using these, the adhesion properties of agrochemicals to crops are extremely improved. However, even though these are used, the adhesion properties to the crops having poor wetting properties, such as cabbage and Japanese long green onion, are not sufficiently satisfying. In particular, recently, drift-reducing spray which has been rapidly spread due to the problems such as environmental pollution related to agrochemical drift is required to be further improved because it leads to less sufficient adhesion properties to crops. In addition, Mixpower (which is a trade name, manufactured by Syngenta: 40% polyoxyethylene alkyl ether and 40% polyoxyethylene alkylphenyl ether), which comprises a nonionic surfactant and has improved adhesion properties to crops, is not preferred from an environmental point of view because it contains polyoxyethylene alkylphenyl ether, which is a suspicious substance as endocrine disrupter, contained in Gramin S and Tokuace although the polyoxyethylene alkylphenyl ether has improved adhesion properties.

In Non-Patent Literature 2, using Neoesterin® (which is a trade name, manufactured by Kumiai Chemical Industry Co., Ltd.: 10% polyoxyethylene fatty acid ester and polyoxyethylene resin acid ester and 20% polyoxyethylene nonylphenyl ether) (in this connection, superscript "RTM" stands for registered trademark) as a spreading agent, chlorphenapyr (insecticide) and acephate (insecticide) were sprayed to control *Plutella xylostella* of cabbage and spray test was conducted using a drift-reducing nozzle, but good results are not obtained.

Non-Patent Literature 3 describes use of sodium bis(2-ethylhexyl)sulfosuccinate as a systemic agent and a spreading agent in terms of its wettability but does not specifically disclose the content, spraying requirements, spray concentration and the like thereof at all.

According to Non-Patent Literature 4, the problem that agrochemical spraying using a drift-reducing nozzle may easily cause spray ununiformity and particularly does not give stable agrochemical efficacy with an agrochemical active ingredient having low systemic properties into agents is pointed out. In addition, it is pointed out that even when an existing spreading agent is used, these problematic points cannot be remedied.

According to Non-Patent Literature 5, when spraying was conducted with a drift-reducing nozzle, no big difference was observed in the adhesion amount and the biological effects of agrochemicals per leaf unit due to the nozzle properties compared with customary nozzles, but it is pointed out that the drift-reducing nozzle slightly inferior to the biological effects only in leaves of cabbage expanded in the vertical direction. In addition, a model experiment using a filter paper was performed, resulting in that the drift-reducing nozzle caused low adhesion uniformity to the longitudinal direction, and it is inferred that this is because the spray particle size is large.

With regard to the technique of evaluation for uniform adhesion of an agrochemical spray aqueous solution to crops, Non-Patent Literature 4 discloses an experiment using a fluorescent pigment but there is no example of surveying effects on addition of the spreading agent and the adjuvant composition.

Patent Literature 1 discloses a spreading agent where fatty acid is added to polyoxyethylene polyoxypropylene alkyl ether as a spreading agent with low foaming for agrochemicals.

In addition, Patent Literature 2 discloses a spreading agent composition for non-aqueous agrochemicals included surfactants, water-soluble organic solvents having a flash point of 70° C. or more and antifoaming agents.

Non-Patent Literature 1: Japan Plant Protection Association, "Annual Inventory of Registered Pesticides and Their Use 2005", pp. 522 to 523, published on October 17th H17

Non-Patent Literature 2: Executive Summary of Lecture in Symposium on Spraying Technique, pp. 81 to 83, published by Japan Plant Protection Association on January 17th H19

Non-Patent Literature 3: Booklet of the Series of RAPISOL A, anionic surfactants, p. 6, June 2003, written by NFO Corporation Non-Patent Literature 4: Program for Protection of Influence of Agrochemical Drift, Fiscal Year H17: Results of Basic Research on Adhesion and Effects, pp. 11 to 47, February H18, Japan Plant Protection Association Non-Patent Literature 5: "Adhesion to Crops and Biological effect of Agrochemical Using Drift-Reducing Nozzle", The 26th Executive summaries of Lecture in Symposium on Agrochemical Formulation and Use, p. 30, October H18

Patent Literature 1: JP 2004-83540 A, pp. 5 to 6

Patent Literature 2: JP 2006-248994 A

DISCLOSURE OF THE INVENTION

Problems to be Solved by the Invention

Drifting reduction in agrochemical spraying is an important problem in view of influence reduction on close growing crops, agricultural workers, ambient inhabitants and ambient environment. As a method for resolving this problem, a drift-reducing nozzle has been developed. It is pointed out that this drift-reducing nozzle shows a superior effect of drift reduction but may not show a stable agrochemical efficacy.

On the other hand, the use of spreading agent and/or adjuvant is established as a technique which facilitates adhesion of agrochemicals to crops and stabilizes agrochemical efficacy. However, it is pointed out that existing spreading agents or adjuvants cannot give sufficient adhesion properties in the case that a drift-reducing nozzle is used (Non-Patent Literatures 2 and 5). Thus, further improvement of the technique for uniformly adhering an agrochemical spray aqueous solution to crops in drift-reducing spray is required. It is an object of the present invention to provide an adjuvant composition capable of uniformly adhering agrochemical components to crops and stabilizing agrochemical efficacies even in the case of drift-reducing spray using, for example, a drift-reducing nozzle, and to provide a control method for stabilizing agrochemical efficacy while reducing drift using it.

Means of Solving the Problems

The present inventors has studied to solve these problems and found that an adjuvant composition of the present invention containing a particular surfactant component in a high concentration makes it possible that an agrochemical spray aqueous solution to which the adjuvant composition is added is uniformly sprayed to target crops and the adjuvant composition allows that uniform adhesion of agrochemical components to young leaves with thick wax and vertical leaves to which adhesion is difficult is improved, and found that particularly, in drift-reducing spray where the volume median diameter of the spray particles is large, the adjuvant composition of the present invention allows that agrochemical components are uniformly adhered to target crops having poor wetting properties and to the above young leaves with thick wax and vertical leaves to stabilize agrochemical efficacies, and the finding has led to the present invention.

That is, the present invention relates to:

(1) An adjuvant composition characterized in that the adjuvant composition contains the following (A) component and (B) component in the following range:
(A) Sodium dialkylsulfosuccinate and polyoxyethylene alkyl ether as surfactant components, the total content of the both being 45 to 85% by mass;
(B) A component for pour-point depressant in an amount of 5 to 40% by mass; relative to the whole adjuvant composition, and the total content of (A) component and (B) component relative to the whole adjuvant composition is 50% by mass or more,
(2) The adjuvant composition according to the above (1), characterized in that the mixture ratio of sodium dialkylsulfosuccinate and polyoxyethylene alkyl ether is 4:1 to 1:5,
(3) The adjuvant composition according to the above (1) or (2), characterized in that the sodium dialkylsulfosuccinate is sodium di(branched alkyl)sulfosuccinate,
(4) The adjuvant composition according to the above (3), characterized in that the sodium di(branched alkyl)sulfosuccinate is sodium bis(2-ethylhexyl)sulfosuccinate,
(5) The adjuvant composition according to any one of the above (1) to (4), characterized in that the alkyl chain of polyoxyethylene alkyl ether is in the range of C11 to C15,
(6) The adjuvant composition according to any one of the above (1) to (5), characterized in that the alkyl chain of polyoxyethylene alkyl ether is in the range of C12 to C14,
(7) The adjuvant composition according to any one of the above (1) to (6), characterized in that the component for pour-point depressant is a glycol and/or water,
(8) The adjuvant composition according to any one of the above (1) to (7), characterized in that the glycol is propylene glycol and/or polyethylene glycol,
(9) The adjuvant composition according to any one of the above (1) to (8), characterized by containing sodium bis(2-ethylhexyl)sulfosuccinate and polyoxyethylene alkyl (C12 to C14) ether,
(10) The adjuvant composition according to any one of the above (1) to (9), wherein the adjuvant composition is for drift-reducing spray,
(11) An agrochemical spray aqueous solution wherein the adjuvant composition according to any one of the above (3) to (10) is added to a diluted liquid containing an agrochemical active ingredient,
(12) The agrochemical spray aqueous solution according to the above (11), wherein the amount of the adjuvant composition to be added is 0.5 to 10 ml per 10 L of the diluted liquid,
(13) The agrochemical spray aqueous solution according to the above (11), where the concentration of the surfactant component in the agrochemical spray aqueous solution is 50 to 1000 ppm,
(14) A method for spraying an agrochemical, wherein the agrochemical spray aqueous solution according to any one of the above (11) to (13) is sprayed using a spreader,
(15) The method for spraying an agrochemical according to the above (14), characterized in that the total volume ratio of the spray particles having a particle size of 100 μm or less is 40% or less when the agrochemical spray aqueous solution is sprayed,
(16) The method for spraying an agrochemical according to the above (15), characterized by using a nozzle for drift-reducing spray where the total volume ratio of the spray particles having a particle size of 100 μm or less is 40% or less when the agrochemical spray aqueous solution is sprayed,
(17) A method for controlling a pest insect, fungus and/or weed, characterized in that the agrochemical spray aqueous solution of the above (11) to (13) is sprayed using a spray nozzle where the volume median diameter of the spray particles is 100 μm or more and the total volume ratio of the spray particles having a particle size of 100 μm or less is 40% or less,
(18) The adjuvant composition according to the above (3), characterized in that the mixture ratio of sodium di(branched alkyl)sulfosuccinate and polyoxyethylene alkyl ether is 4:1 to 1:10,
(19) An adjuvant composition, wherein:
(A) Sodium di(branched C8 to C12 alkyl)sulfosuccinate and polyoxyethylene C11 to C15 alkyl ether (the polymerization degree of the polyoxyethylene is 3 to 15) are contained as surfactant components, the total content of the both is 45 to 85% by mass relative to the whole adjuvant composition, the content of said polyoxyethylene C11 to C15 alkyl ether is 20 to 70% by mass, and the mass ratio of sodium di(branched C8 to C12 alkyl)sulfosuccinate:polyoxyethylene C11 to C15 alkyl ether is in the range of 4:1 to 1:10;
(B) C2 to C4 alkylene glycol or/and water is contained in an amount of 5 to 35% by mass, as a component for pour-point depressant;
and the rest is an optional component other than the above,
(20) The adjuvant composition according to the above (19), wherein the sodium di(branched C8 to C12 alkyl)sulfosuccinate is sodium bis(2-ethylhexyl)sulfosuccinate, the polymerization degree of the polyoxyethylene in the polyoxyethylene C11 to C15 alkyl ether is 7 to 12, and the C2 to C4 alkylene glycol is propylene glycol,
(21) The adjuvant composition according to the above (19) or (20), wherein the content of the C2 to C4 alkylene glycol or the propylene glycol is 5 to 25% by mass,

(22) The adjuvant composition according to the above (19) or (20), wherein C2 to C4 alkylene glycol and water are contained as components for pour-point depressant, the total content of the both is 5 to 35% by mass relative to the whole adjuvant composition, and the ratio of C2 to C4 alkylene glycol:water is 7:3 to 4:6,

(23) The agrochemical spray aqueous solution wherein agrochemical active ingredient, sodium di(branched C8 to C12 alkyl)sulfosuccinate, polyoxyethylene alkyl ether, C2 to C4 alkylene glycol and water are contained, the concentration of the agrochemical active ingredient is 5 to 1000 ppm, the total concentration of sodium di(branched alkyl)sulfosuccinate and polyoxyethylene alkyl ether as surfactant components (A) is 150 to 300 ppm relative to the whole spray aqueous solution, and the concentration of the C2 to C4 alkylene glycol is 20 to 100 ppm relative to the whole spray aqueous solution.

Effect of the Invention

The adjuvant composition of the present invention is added to a diluted liquid of an agrochemical to give an agrochemical spray aqueous solution, whereby the agrochemical spray aqueous solution can be uniformly sprayed and adhered to target crops. In particular, in drift-reducing spray where the volume median diameter of the spray particles are large, said composition has the effect that uniform adhesion of an agrochemical component to target crops having poor wetting properties is improved to stabilize agrochemical efficacy.

BEST MODE FOR CARRYING OUT THE INVENTION

Hereinafter, the adjuvant composition of the present invention, the agrochemical spray aqueous solution to which it is added, the method for spraying the agrochemical spray aqueous solution thereof and the controlling method for stabilizing the agrochemical efficacies while reducing drift when spraying agrochemical will be more specifically explained.

The adjuvant composition is characterized in that the adjuvant composition contains the following (A) component and (B) component in the following range:
(A) Sodium dialkylsulfosuccinate and polyoxyethylene alkyl ether as surfactant components, the total content of the both being 45 to 85% by mass;
(B) A component for pour-point depressant in an amount of 5 to 40% by mass;
relative to the whole adjuvant composition, and the total content of (A) component and (B) component is 50% by mass or more relative to the whole adjuvant composition.

The adjuvant composition of the present invention improves uniform spray properties and adhesion properties of agrochemical spray aqueous solution to target crops, and particularly improves adhesion of agrochemical components to target crops having poor wetting properties such as cabbage and long green onion even in drift-reducing spray where the volume median diameter of the spray particles is large. Therefore the adjuvant composition of the present invention is particularly suitable for drift-reducing spray. In the present invention, the above effects can be attained by combining sodium dialkylsulfosuccinate with polyoxyethylene alkyl ether and being 45% to 85% by mass of the total content of the both.

That is, the adjuvant composition of the present invention containing, as surfactant components of (A) component, sodium dialkylsulfosuccinate and polyoxyethylene alkyl ether in a particular ratio of the total content and also containing (B) component (component for pour-point depressant) makes it possible highly uniform adhesion properties of agrochemicals which cannot be achieved by conventional and known spreading agents where the above anionic and nonionic surfactants are combined. The total content of (A) component is preferably 45 to 85% by mass and more preferably 50 to 80% by mass. Further preferable is 60 to 80% by mass.

In the adjuvant composition of the present invention, the content of sodium dialkylsulfosuccinate can be optionally determined by such a combination of polyoxyethylene alkyl ether that the total content of the both is in the above range. There is a case that the physical properties of characteristic features of anionic surfactant are not utilized when the content of the sodium dialkylsulfosuccinate is below 4% by mass, and flowability may be poor when the content is more than 70% by mass, whereby the preferable range thereof is 5 to 70% by mass, more preferably 7 to 55% by mass, further preferably 10 to 55% by mass and most preferably 15 to 55% by mass, relative to the whole adjuvant composition.

In addition, in the adjuvant composition of the present invention, the content of polyoxyethylene alkyl ether can be also optionally determined by such a combination of sodium dialkylsulfosuccinate that the total content of the both is in the above range. The content of polyoxyethylene alkyl ether is preferably 9 to 80% by mass and more preferably 10 to 80% by mass, relative to the whole adjuvant composition. The characteristic features of nonionic surfactant are not easily appeared when the content thereof is below 9% by mass, and the addition of dialkylsulfosuccinic acid in the optimum amount range may be disabled when the content is more than 80% by mass. The content of polyoxyethylene alkyl ether is more preferably 20 to 70% by mass and further preferably 20 to 65% by mass, relative to the whole adjuvant composition. Under this condition, said adjuvant composition can demonstrate the optimum uniform adhesive performance. Further, when the polymerization degree of polyoxyethylene in polyoxyethylene alkyl ether is 9 or more, the pour-point is around 1 to 10° C. and therefore the content is preferably 80% by mass or less for preparation.

The mixture ratio of sodium dialkylsulfosuccinate and polyoxyethylene alkyl ether can be optionally varied respectively in the range of 1 to 84% by mass as long as the total content of the both is in the range of 45 to 85% by mass, and preferably, they are preferably used in such a range that each content is in the range described above. More preferably, the mixture ratio (mass ratio) of sodium dialkylsulfosuccinate and polyoxyethylene alkyl ether is 4:1 to 1:10. Said ratio is further preferably 4:1 to 1:5 and most preferably 3:1 to 1:4.

In adjuvant composition of the present invention, alkyl of sodium dialkylsulfosuccinate to be used may be any of, for example, linear C8 to C12 alkyl or branched C8 to C12 alkyl. The examples thereof include an n-octyl group, an n-nonyl group, a decanyl group, an undecanyl group, a dodecanyl group, a 2-ethyl hexyl group or the like. Among them, sodium di(branched C8 to C12 alkyl)sulfosuccinate having a high wettability is preferable, and further among them, sodium bis(2-ethylhexyl)sulfosuccinate is preferable. The purity of sodium dialkylsulfosuccinate to be used is preferably high and it is preferably 65% or more as an active ingredient because sodium dialkylsulfosuccinate having a higher content of impurities leads to poor adhesion properties to target crops. Typical examples of sodium dialkylsulfosuccinate include RAPISOL® A90 (which is a trade name, manufactured by NFO Corporation, containing 90% sodium bis(2-ethylhexyl)sulfosuccinate and 3.7% methanol), Airroll® CT-1L (which is a trade name, manufactured by TOHO Chemical Industry Co., LTD.: containing 70% sodium bis(2- ethylhexyl)sulfosuccinate), Newkalgen EP-70G (which is a trade name manufactured by Takemoto Oil & Fat Co., Ltd.: containing 70% sodium bis(2-ethylhexyl)sulfosuccinate) and the like.

The polyoxyethylene alkyl ether to be used in the present invention can be used that having various alkyl chains, and among them, preferable thereof is polyoxyethylene alkyl ether having a carbon atom number of alkyl chains ranging from C11 to C15. They may be one kind of carbon numbers or, two or more kinds of carbon numbers as a mixture. The examples thereof specifically include a mixture of polyoxyethylene alkyl ethers having a C11 to C15 alkyl chain, a mixture of polyoxyethylene alkyl ethers having a C12 to C14 alkyl chain, only polyoxyethylene alkyl ether having a C13 alkyl chain and the like. Among them, a mixture of polyoxyethylene alkyl ethers having a C12 to C14 alkyl chain is particularly preferable for improvement of the uniform adhesion properties to uniformly adhere agrochemicals to target crop. In addition, the polymerization degree of polyoxyethylene chain has a great influence on HLB (Hydrophile-Lipophile Balance) indicating oil-water characteristic values of surfactants and thus it is an important factor of wettability and the like. Polyoxyethylene has a various polymerization degree, and polyoxyethylene having any degree can be used as long as the degree is 2 or more. Among them, the polymerization degree leading to superior adhesion properties to target crops is 3 or more and more preferably about 3 to 12. In addition, the polymerization degree is preferably 7 or more and further preferably 7 to 12, in some cases. Typical examples of polyoxyethylene alkyl ether include Pegnol® T-3 (which is a trade name, manufactured by TOHO Chemical Industry Co., LTD.: the polyoxyethylene polymerization degree=3), Pegnol® ST-5 (which is a trade name, manufactured by TOHO Chemical Industry Co., LTD.: the polyoxyethylene polymerization degree=5), Pegnol® ST-7 (which is a trade name, manufactured by TOHO Chemical Industry Co., LTD.: the polyoxyethylene polymerization degree=7), Pegnol® ST-9 (which is a trade name, manufactured by TOHO Chemical Industry Co., LTD.: the polyoxyethylene polymerization degree=9), Pegnol™ ST-12 (which is a trade name, manufactured by TOHO Chemical Industry Co., LTD.: the polyoxyethylene polymerization degree=12) and the like. Among them, preferable are Pegnol® ST-7, Pegnol® ST-9 and Pegnol® ST-12 where the polymerization degree of polyoxyethylene is 7 or more. In this connection, Pegnol® described above is polyoxyethylene alkyl (a mixture of C12 to C14) ether.

The component for pour-point depressant in the adjuvant composition of the present invention means a component which can provide flowability by lowering the pour-point (melting point) of the composition; and in the composition, addition of about 5 to 40% by mass thereof is necessary, addition of about 5 to 35% by mass is preferable and 5 to 30% by mass is more preferable. This component has the ability to dissolve and fluidize dialkylsulfosuccinic acid which is a gel compound having no flowability, and can be any substance as long as it has an effect of lowering the pour-point of polyoxyethylene alkyl ether and of suppressing its freezing in wintertime. Examples thereof include glycols, alcohols, water and the like. The content of these components for pour-point depressant may be about 5 to 40% by mass relative to the whole adjuvant composition, however, the range of 5 to 30% by mass is appropriate, and 10 to 25% by mass is further preferable.

Preferable examples of the glycols include C2 to C4 alkylene glycol, polyalkylene glycol and the like, and specifically include propylene glycol, polyethylene glycol and the like. In addition, examples of the alcohols include alcohols such as C1 to C4 alcohol, and specifically include methanol, isopropylalcohol, ethanol and the like. Among them, preferable are glycols having a lower toxicity and a lower risk of dissolving the agrochemical active ingredient when mixed with the agrochemical formulation and of easily causing phytotoxicity by damaging crop surfaces which is observed in alcohols such as methanol, and also having a higher flash point: for example, C2 to C4 alkylene glycol or/and water. Among them, propylene glycol is particularly preferable. The components for pour-point depressant may be used either alone or in combination of two or more kinds. The adjuvant composition of the present invention preferably contains a glycol (preferably C2 to C4 alkylene glycol and more preferably propylene glycol) in the range of 5 to 25% by mass, preferably 5 to 20% by mass and further preferably 7 to 15% by mass relative to said whole composition. In addition, the combination use of glycols and water is more preferable. For example, the combination use of propylene glycol and water is the most appropriate because it has the effect of lowering the pour-point of the adjuvant composition by mixing the both with the surfactant component and therefore the composition does not freeze in cold climates (−15° C. or more). When glycols and water are used in combination as the component for pour-point depressant, the total content thereof relative to the whole adjuvant composition of the present invention may be in the range of the above 5 to 40% by mass and preferably 5 to 30% by mass, and the ratio of glycols and water is preferably 8:2 to 3:7 and further preferably 7:3 to 4:6. The water content in the adjuvant composition of the present invention may be about 0 to 20% by mass relative to the whole adjuvant composition, and it is preferably about 5 to 15% by mass in the case of the combination use with glycols.

The concentration of the agrochemical active ingredient contained in said agrochemical spray aqueous solution is not particularly limited but about 5 to 1000 ppm, preferably 25 to 1000 ppm and further preferably 25 to 500 ppm, relative to said whole spray aqueous solution.

In the adjuvant composition of the present invention, the following other surfactants may be also mixed as long as they do not impair the adhesion state of the agrochemical active ingredient. Examples thereof include nonionic surfactants such as polyoxyethylene polyoxypropylene copolymer, polyoxyethylene alkylaryl ether, polyoxyethylene styrylphenyl ether, polyoxyethylene phenyl ether polymer, polyoxyethylene alkylene aryl phenyl ether, polyoxyethylene polyoxypropylene block polymer and anionic surfactants such as polyoxyethylene styrylphenyl ether sulfate, lignin sulfonate, alkylaryl sulfonate and alkylnaphthalene sulphonate. These other surfactants are usually preferably used in the range of about 0 to 20% by mass. Combination use is preferred in some cases, where they may be usually added within the above range and more preferably 5 to 10% by mass.

The total content of the above (A) component and (B) component in the adjuvant composition of the present invention is preferably at least 50% by mass or more, more preferably 70% by mass or more and further preferably 90% by mass or more, relative to the whole adjuvant composition. The upper limit thereof may be 100% by mass but practically 99% by mass or less. Other components other than the above (A) component and (B) component in the adjuvant composition are components such as optional component and solvent contained in the surfactant component, and they may be contained in the range of 0 to 50% by mass, preferably 0 to 30% by mass and further preferably 0 to 10% by mass. Examples of the optional component include other surfactant components described above and the like.

The adjuvant composition of the present invention allows the agrochemical active ingredient to uniformly adhere to crops even in the case of using a nozzle for drift-reducing spray, and in addition, a customary nozzle to be usually used.

The adjuvant composition of the present invention can be used by adding it to a diluted liquid containing an agrochemical active ingredient when an agrochemical spray aqueous solution is made. The diluted liquid containing an agrochemical active ingredient described here means a diluted liquid of an already-made agrochemical formulation usually diluted with water, and hereinafter, it is also referred to as a diluted liquid of agrochemical formulation. Examples of the agrochemical formulation include flowables, emulsions, wettable powders, water dispersible granules, microcapsules and the like, and any of them can be used as long as it can be sufficiently dispersed and emulsified with dilution water. The adjuvant composition of the present invention can be also used for a diluent of any agrochemical formulation. In addition, the agrochemical spray aqueous solution utilizing the adjuvant composition of the present invention can be made by adding the adjuvant composition of the present invention to an agrochemical formulation in advance and then by adding water, or by adding the adjuvant composition of the present invention to a diluted liquid of an agrochemical formulation afterward. The addition amount of the adjuvant composition of the present invention is optionally controlled to some extent by fully considering the adhesion properties to target crops, so the addition amount can be determined to be more for rice, wheat, cabbage and the like to which adhesion is poor and it can be determined to be less for cucumber and the like to which adhesion is good, however, it is preferable to add the adjuvant composition in an amount of 0.5 to 10 ml per 10 L of the diluted liquid, and it is more preferable to add the adjuvant composition in an amount of 1 to 3 ml per 10 L of the diluted liquid.

The surfactant concentration in the agrochemical spray aqueous solution means the total concentration of dialkylsulfosuccinic acid and polyoxyethylene alkyl ether and in addition the surfactant component contained, and it has an effect on improvement of adhesion properties of the agrochemical component to target crops and stabilization of the agrochemical efficacy. The concentration varies according to spray conditions such as the kind of target crop and the spray nozzle, and it is preferably 50 to 1000 ppm. It is further preferably 100 to 800 ppm. In the case of spraying using a drift-reducing nozzle, the concentration of 150 to 800 ppm is preferable. In said spray aqueous solution, the total concentration of dialkylsulfosuccinic acid (preferably di(branched C8 to C12 alkyl)sulfosuccinic acid) and polyoxyethylene alkyl ether (the polymerization degree is preferably 3 to 12 and more preferably 7 to 12; the carbon atom number of the alkyl group is preferably 11 to 15 and more preferably 12 to 14) is usually about 150 to 300 ppm and more preferably 200 to 270 ppm, relative to the whole spray aqueous solution. In addition, the concentration of glycols (preferably C2 to C4 alkylene glycol) relative to the whole spray aqueous solution is preferably about 20 to 100 ppm.

The agrochemical spray aqueous solution where the adjuvant composition is added to the diluted liquid of the agrochemical formulation mentioned above can be sprayed, as it is, by a spraying method using a usual spreader. Examples of the spraying method include spraying methods by power sprayer, boom sprayer, speed sprayer and unmanned helicopter.

In the present invention, drift-reducing spray means spraying under the conditions that the total volume ratio of spray particles having a particle size of 100 μm or less is 40% or less (from the table II-2 in Agrochemical Spraying Technique, Japan Plant Protection Association, March 2nd H10, p. 28). Examples of the method of drift-reducing spray include the following:
1) A usual nozzle for spraying is used and the spray pressure is 1.0 to 2.0 MPa or less;
2) A nozzle for drift reduction is used (the spray pressure is 1.0 to 2.0 MPa).

The drift-reducing nozzle described in the present invention means a nozzle where the total volume ratio of spray particles having a particle size of 100 μm or less is 40% or less. In addition, more preferably in using nozzle, not only suppressing the drift with particles where the total volume ratio of spray particles having a particle size of 100 μm or less is 40% or less but also enlarging the spray particle size are one of the effective means, and therefore it is desirable to spray using a drift-reducing nozzle where the volume median diameter (Volume Median Diameter: particle size of 50% of the cumulative values of the spray particles) of the spray particles is 100 μm or more and the total volume ratio of the spray particles of 100 μm or less is 40% or less. Examples of the drift-reducing nozzle include Kirinashi ES Tip (which is a trade name, manufactured by YAMAHO Industry Co., Ltd.: the volume median diameter is 280 to 345 μm and the total volume ratio of the spray particles of 100 μm or less is 5 to 15% (1.5 MPa)), Kirinashi KS Tip (which is a trade name, manufactured by YAMAHO Industry Co., Ltd.: the volume median diameter is 259 to 452 μm and the total volume ratio of the spray particles of 100 μm or less is 4 to 7% (1.5 MPa)), Saving Nozzle (which is a trade name, manufactured by YAMAHO Industry Co., Ltd.: the volume median diameter is 100 μm and the total volume ratio of the spray particles of 100 μm or less is 35% (1.0 MPa)) and the like.

The control method stabilizing the agrochemical efficacy while reducing drift in agrochemical spraying can be achieved by drift reduction using a drift-reducing nozzle and by utilizing the adjuvant composition of the present invention. The addition of the adjuvant composition of the present invention allows that an agrochemical component adheres more uniformly even when the particle size of the spray particles is larger by using a drift-reducing nozzle, whereby the agrochemical efficacy can be stabilized.

The adjuvant composition of the present invention and the spraying method thereof can be applied to the crops for which each of agrochemical formulations (fungicide, insecticide, herbicide and the like) is registered to be used and, for example, can be used with fungicide, insecticide, herbicide and the like for grains such as rice and wheat, vegetables such as cabbage, potato, cucumber and eggplant and fruit trees such as tea, apple and citrus.

As the agrochemical active ingredient which can be adaptive to the adjuvant composition of the present invention, for example, agrochemical active ingredients described in "Annual Inventory of Registered Pesticides and Their Use 2006, published by Japan Plant Protection Association, October 19 H18" can be used, and they can be used in combination of one kind or more kinds thereof by the method in the category according to agrochemical registration. Examples of the active ingredient in those agrochemical formulations include, as for insecticide, acrinathrin, acequinocyl, acetamiprid, acephate, amitraz, alanycarb, allethrin, isoxathion, imidacloprid, indoxacarb MP, esfenvalerate, ethiofencarb, ethiprole, ethylthiometon, etoxazole, etofenprox, emamectin benzoate, levamisole hydrochloride, oxamyl, cadusafos, cartap hydrochloride, carbosulfan, clothianidin, clofentezine, chromafenozide, chlorpyrifos, chlorfenapyr, chlorfluazuron, cycloprothrin, dinotefuran, cyfluthrin, dimethoate, spinosad, diazinon, thiacloprid, thiamethoxam, thiodicarb, thiocyclam oxalate, tebufenozide, tebufenpyrad, tefluthrin, teflubenzuron, tralomethrin, tolfenpyrad, novaluron, halfenprox, bifenazate, bifenthrin, pymetrozine, pyraclofos, pyridafenthion, pyridaben, pyridalyl, pyriproxyfen, pyrimidifen, pirimiphos-methyl, pyrethrins, fipronil, phenisobromolate, fenothiocarb, fluacrypyrim, flucythrinate, fluvalinate, flufenoxuron, propaphos, profenofos, hexythiazox, permethrin, bensultap, benzoepin, benfuracarb, beauveria bassiana, beauveria brongniartii, phosalone, machine oil, malathion, mesulfenfos, methomyl, methoxyfenozide, lufenuron, BPMC, BT (*Bacillus thuringiensis* fungi), methidathion, fenitrothion, isoprocarb, fenthion, NAC and the like; and they can appropriately selected according to crops and pest insects. In addition, they can be used in combination with a fungicide.

Examples of the active ingredient in those agrochemical formulations include, as for fungicide, include acibenzolar-s-methyl, azoxystrobin, amobam, sulfur, isoprothiolane, ipconazole, iprodione, iminoctadine albesilate, iminoctadine acetate, imibenconazole, echlomezole, oxadixyl, oxytetracycline, oxpoconazole-fumarate, oxolinic acid, kasugamycin, carpropamid, chinomethionat, captan, kresoxim-methyl, chloroneb, cyazofamid, diethofencarb, diclocymet, diclomezine, dithianon, zineb, difenoconazole, cyflufenamid, diflumrtorim, cyproconazole, cyprodinil, simeconazole, dimethomorph, cymoxanil, pseudomonad fluorescens, pseudomonad CAB-02, ziram, wettable sulfur, streptomycin, potassium hydrogen carbonate, sodium hydrogen carbonate, thiadiazine, tiadinil, thiabendazole, thiuram, thiophanate-methyl, thifluzamide, tecloftalam, tetraconazole, tebuconazole, copper, triadimefon, triazine, trichoderma atroviride, tricyclazole, triflumizole, trifloxystrobin, triforine, tolclofos-methyl, bacillus subtilis, validamycin, bitertanol, hydroxyisoxazole, pyrazophos, pyrifenox, pyrimethanil, pyroquilon, famoxadone, fenarimol, fenoxanil, ferimzone, fenbuconazole, fenhexamid, fthalide, furametpyr, fluazinam, fluoroimide, fludioxonil, flusulfamide, flutolanil, procymidone, propamocarb hydrochloride, propiconazole, propineb, probenazole, hexaconazole, benomyl, pefurazoate, pencycuron, boscalid, fosetyl, polycarbamate, manzeb, maneb, myclobutanil, mildiomycin, methasulfocarb, metominostrobin, mepanipyrim, organic copper, zinc sulfate, copper sulfate, edifenphos, iprobenfos, chlorothalonil and the like; and they can appropriately selected according to crops and pest insects. In addition, they can be used in combination with an insecticide.

Examples of the active ingredient in those agrochemical formulations include, as for herbicide, include ioxynil, azimsulfuron, asulam, atrazine, anilofos, alachlor, isouron, isoxaben, imazaquin, imazapyr, imazosulfuron, indanofan, esprocarb, ethoxysulfuron, etobenzanid, chlorate, oxadiazon, oxadiargyl, oxaziclomefone, orthobencarb, oryzalin, cafenstrole, carfentrazone-ethyl, karbutilate, quizalofop-methyl, cumyluron, glyphosate ammonium salt, glyphosate isopropylamine salt, glyphosate potassium salt, glyphosate trimesium salt, glufosinate, clethodim, clomeprop, chlorphthalim, cyanazine, cyanate, cyclosulfamuron, diquat, dithiopyr, siduron, cinosulfuron, cyhalofop-butyl, diflufenican, dimethametryn, dimethenamid, simetryn, cinmethylin, sethoxydim, daimuron, dazomet, thifensulfuron-methyl, desmedipham, tetrapion, thenylchlor, tepraloxydim, triaziflam, triclopyr, trifluralin, trifloxysulfuron-sodium, napropamide, nicosulfuron, paraquat, halosulfuron methyl, bilanafos, bispyribac-sodium, bifenox, pyrazoxyfen, pyrazosulfuron methyl, pyrazolate, pyrafulphenthion, pyriftalid, pyributicarb, pyriminobac-methyl, phenothiol, fentrazamide, phenmedipham, butachlor, butamifos, flazasulfuron, fluazifop, fluthiacet-methyl, flumioxazin, pretilachlor, prodiamine, propyzamide, bromacil, prometryn, bromobutide, florasuram, bethrodine, bensulfuron-methyl, benzofenap, benzobicyclon, bentazon sodium salt, benthiocarb, pendimethalin, pentoxazone, benfuresate, metamitron, metsulfuron-methyl, metolachlor, metribuzin, mefenacet, molinate, linuron, rimsulfuron, lenacil, ACN, simazine, dichlobenil, chlorthiamid, diuron, propanil, MCP, MCP isopropylamine salt, MCPB, MCPP, MDBA, MDBA isopropylamine salt, PAC, SAP, 2, 4 PA and the like.

The adjuvant composition of the present invention can be specifically produced according to the following process, but a similar machine and process can be applied and thus the process is not limited.

Process: Sodium dialkylsulfosuccinate, polyoxyethylene alkyl ether and a component for pour-point depressant are put in a pot and then if needed, a surfactant such as a polyoxyethylene polyoxypropylene copolymer is put therein and the mixture is dissolved by mixing at an ordinary temperature or with heating to obtain a desired adjuvant composition.

The adjuvant composition of the present invention obtained above can be filled in a container and stored, according to necessity. Said container may be appropriately selected from plastic bottles and the like widely used in view of drop test and the like. Specifically, examples thereof include multilayer nylon bottles and the like. A preferable example thereof includes a multilayer nylon bottle (manufactured by Hokusan Co., Ltd.) comprised of high density polyethylene (containing calcium carbonate)/nylon. The adjuvant composition of the present invention filled in said bottle is preferable because it has a superior durability for a long period of time. In addition, "/" described in the section of material quality for bottles described above means that the components are joined with an adhesive.

EXAMPLES

Next, the present invention will be more specifically explained with reference to the Examples, but the present invention is not limited thereto.

Example 1

Into a 200 ml flask, 30 parts by mass of RAPISOL® A90 (which is a trade name, manufactured by NFO Corporation: containing 90% sodium bis(2-ethylhexyl)sulfosuccinate and 3.7% methanol), 30 parts by mass of Pegnol® ST-9 (which is a trade name, manufactured by TOHO Chemical Industry Co., LTD.: containing 100% polyoxyethylene alkyl (C12 to 14) ether and having a polyoxyethylene polymerization degree of 9), 10 parts by mass of propylene glycol and 10 parts by mass of tap water were put, and fused by mixing at 60° C. to obtain an adjuvant composition (33.8% sodium dialkylsulfosuccinate and 37.5% polyoxyethylene alkyl (C12 to 14) ether).

Example 2

In a 200 ml flask, 20 parts by mass of RAPISOL® A90 (which is a trade name, manufactured by NFO Corporation: containing 90% sodium bis(2-ethylhexyl)sulfosuccinate and 3.7% methanol), 60 parts by mass of Pegnol® ST-9 (which is a trade name, manufactured by TOHO Chemical Industry Co., LTD.: containing 100% polyoxyethylene alkyl (C12 to 14) ether and having a polyoxyethylene polymerization degree of 9), 10 parts by mass of propylene glycol and 10 parts by mass of tap water were put, and fused by mixing at 60° C. to obtain an adjuvant composition (18% sodium dialkylsulfosuccinate and 60% polyoxyethylene alkyl (C12 to 14) ether).

Example 3

In a 200 ml flask, 60 parts by mass of RAPISOL® A90 (which is a trade name, manufactured by NFO Corporation: containing 90% sodium bis(2-ethylhexyl)sulfosuccinate and 3.7% methanol), 20 parts by mass of Pegnol® ST-9 (which is a trade name, manufactured by TOHO Chemical Industry Co., LTD.: containing 100% polyoxyethylene alkyl (C12 to 14) ether and having a polyoxyethylene polymerization degree of 9), 10 parts by mass of propylene glycol and 10 parts by mass of tap water were put, and fused by mixing at 60° C. to obtain an adjuvant composition (54% sodium dialkylsulfosuccinate and 20% polyoxyethylene alkyl (C12 to 14) ether).

Example 4

In a 200 ml flask, 20 parts by mass of RAPISOL® A90 (which is a trade name, manufactured by NFO Corporation: containing 90% sodium bis(2-ethylhexyl)sulfosuccinate and 3.7% methanol), 60 parts by mass of Pegnol® ST-3 (which is a trade name, manufactured by TOHO Chemical Industry Co., LTD.: containing 100% polyoxyethylene alkyl (C12 to 14) ether and having a polyoxyethylene polymerization degree of 3), 10 parts by mass of propylene glycol and 10 parts by mass of tap water were put, and fused by mixing at 60° C. to obtain an adjuvant composition (18% sodium dialkylsulfosuccinate and 60% polyoxyethylene alkyl (C12 to 14) ether).

Example 5

In a 200 ml flask, 20 parts by mass of RAPISOL® A90 (which is a trade name, manufactured by NFO Corporation: containing 90% sodium bis(2-ethylhexyl)sulfosuccinate and 3.7% methanol), 40 parts by mass of Pegnol® ST-5 (which is a trade name, manufactured by TOHO Chemical Industry Co., LTD.: containing 100% polyoxyethylene alkyl (C12 to 14) ether and having a polyoxyethylene polymerization degree of 5), 10 parts by mass of propylene glycol and 10 parts by mass of tap water were put, and fused by mixing at 60° C. to obtain an adjuvant composition (22.5% sodium dialkylsulfosuccinate and 50% polyoxyethylene alkyl (C12 to 14) ether).

Example 6

In a 200 ml flask, 20 parts by mass of RAPISOL® A90 (which is a trade name, manufactured by NFO Corporation: containing 90% sodium bis(2-ethylhexyl)sulfosuccinate and 3.7% methanol), 50 parts by mass of Pegnol® ST-12 (which is a trade name, manufactured by TOHO Chemical Industry Co., LTD.: containing 100% polyoxyethylene alkyl (C12 to 14) ether and having a polyoxyethylene polymerization degree of 12), 10 parts by mass of Newkalgen 5050PB (which is a trade name, manufactured by Takemoto Oil & Fat Co., Ltd.: polyoxyethylene polyoxypropylene copolymer), 10 parts by mass of propylene glycol and 10 parts by mass of tap water were put, and fused by mixing at 60° C. to obtain an adjuvant composition (18% sodium dialkylsulfosuccinate and 50% polyoxyethylene alkyl (C12 to 14) ether).

Example 7

In a 200 ml flask, 30 parts by mass of RAPISOL® A90 (which is a trade name, manufactured by NFO Corporation: containing 90% sodium bis(2-ethylhexyl)sulfosuccinate and 3.7% methanol), 30 parts by mass of Pegnol® ST-3 (which is a trade name, manufactured by TOHO Chemical Industry Co., LTD.: containing 100% polyoxyethylene alkyl (C12 to 14) ether and having a polyoxyethylene polymerization degree of 3), 10 parts by mass of propylene glycol and 10 parts by mass of tap water were put, and fused by mixing at 60° C. to obtain an adjuvant composition (33.8% sodium dialkylsulfosuccinate and 37.5% polyoxyethylene alkyl (C12 to 14) ether).

Example 8

In a 200 ml flask, 20 parts by mass of Newkalgen EP-70G (which is a trade name, manufactured by Takemoto Oil & Fat Co., Ltd.: containing 70% sodium bis(2-ethylhexyl)sulfosuccinate), 50 parts by mass of Pegnol® ST-5 (which is a trade name, manufactured by TOHO Chemical Industry Co., LTD.: containing 100% polyoxyethylene alkyl (C12 to 14) ether having a polyoxyethylene polymerization degree of 5), 20 parts by mass of propylene glycol and 10 parts by mass of tap water were put, and fused by mixing at 60° C. to obtain an adjuvant composition (14% sodium dialkylsulfosuccinate and 50% polyoxyethylene alkyl (C12 to 14) ether).

Example 9

In a 200 ml flask, 20 parts by mass of Newkalgen EP-70G (which is a trade name, manufactured by Takemoto Oil & Fat Co., Ltd.: containing 70% sodium bis(2-ethylhexyl)sulfosuccinate), 50 parts by mass of Pegnol® ST-3 (which is a trade name, manufactured by TOHO Chemical Industry Co., LTD.: containing 100% polyoxyethylene alkyl (C12 to 14) ether and having a polyoxyethylene polymerization degree of 3), 20 parts by mass of propylene glycol and 10 parts by mass of tap water were put, and fused by mixing at 60° C. to obtain an adjuvant composition (14% sodium dialkylsulfosuccinate and 50% polyoxyethylene alkyl (C12 to 14) ether).

Example 10

In a 200 ml flask, 10 parts by mass of Newkalgen EP-70G (which is a trade name, manufactured by Takemoto Oil & Fat Co., Ltd.: containing 70% sodium bis(2-ethylhexyl)sulfosuccinate), 70 parts by mass of Newkalgen D-1203 (which is a trade name, manufactured by Takemoto Oil & Fat Co., Ltd.: containing 100% polyoxyethylene alkyl (C13) ether) and 20 parts by mass of propylene glycol were put, and mixed at ordinary temperature to obtain an adjuvant composition (7% sodium dialkylsulfosuccinate and 70% polyoxyethylene alkyl (C13) ether).

Comparative Example 1

Shin Gramin® (which is a trade name, manufactured by Sankyo Agro Co., Ltd.: 10% polyoxyethylene dodecyl ether, 10% polyoxyethylene nonylphenyl ether and 12% Calcium Ligninsulfonate): 100 parts by mass.

Comparative Example 2

Shin Rinoh® (which is a trade name, manufactured by Nihon Nohyaku Co Ltd.: 10% polyoxyethylene nonylphenyl ether and 20% Calcium Ligninsulfonate): 100 parts by mass.

Comparative Example 3

NEEDS® (which is a trade name, manufactured by Kao Corporation: 44% polyoxyethylene fatty acid ester and 18% polynaphthylmethanesulfonic acid dialkyl dimethyl ammonium): 100 parts by mass.

Comparative Example 4

APPLAUCH® BI (which is a trade name, manufactured by Kao Corporation: 50% polyoxyethylene hexitan fatty acid ester): 100 parts by mass.

Comparative Example 5

Newkalgen A-41B (which is a trade name, manufactured by Takemoto Oil & Fat Co., Ltd.: 70% sodium alkylbenzene sulphonate): 100 parts by mass.

Comparative Example 6

Newkalgen D-945 (which is a trade name, manufactured by Takemoto Oil & Fat Co., Ltd.: 100% polyoxyethylene sorbitan alkylate): 100 parts by mass.

Comparative Example 7

Newkalgen CL-H (which is a trade name, manufactured by Takemoto Oil & Fat Co., Ltd.: 80% polyoxyethylene nonylphenyl ether): 100 parts by mass.

Comparative Example 8

In a 200 ml flask, 9 parts by mass of RAPISOL® A90 (which is a trade name, manufactured by NFO Corporation: containing 90% sodium bis(2-ethylhexyl)sulfosuccinate and 3.7% methanol), 31 parts by mass of Pegnol® ST-9 (which is a trade name, manufactured by TOHO Chemical Industry Co., LTD.: containing 100% polyoxyethylene alkyl (C12 to 14) ether and having a polyoxyethylene polymerization degree of 9), 10 parts by mass of propylene glycol and 50 parts by mass of tap water were put, and fused by mixing at 60° C. to obtain a composition (8.1% sodium bis(2-ethylhexyl)sulfosuccinate and 31% polyoxyethylene alkyl (C12 to 14) ether).

Comparative Example 9

In a 200 ml flask, 31 parts by mass of RAPISOL® A90 (which is a trade name, manufactured by NFO Corporation: containing 90% sodium bis(2-ethylhexyl)sulfosuccinate and 3.7% methanol), 20 parts by mass of propylene glycol and 49 parts by mass of tap water were put, and fused by mixing at 60° C. to obtain a composition (30.1% sodium bis(2-ethylhexyl)sulfosuccinate).

Comparative Example 10

In a 200 ml flask, 31 parts by mass of Pegnol ST-9 (which is a trade name, manufactured by TOHO Chemical Industry Co., LTD.: containing 100% polyoxyethylene alkyl (C12 to 14) ether and having a polyoxyethylene polymerization degree of 9), 20 parts by mass of propylene glycol and 49 parts by mass of tap water were put, and mixed at ordinary temperature to obtain a composition (31% polyoxyethylene alkyl (C12 to 14) ether).

Comparative Example 11

Tokuace® (which is a trade name, manufactured by Sankyo Agro Co., Ltd.: 9% sodium dialkylsulfosuccinate and 31% polyoxyethylene alkylphenyl ether): 100 parts by mass.

Comparative Example 12

RABIDEN® 3S (which is a trade name: 1.4% sodium dioctylsulfosuccinate, 8% polyoxyethylene alkyl ether and 3% polyoxyethylene fatty acid ester): 100 parts by mass.

Comparative Example 13

RAPISOL® A90 (which is a trade name, manufactured by NFO Corporation: containing 90% sodium bis(2-ethylhexyl)sulfosuccinate and 3.7% methanol): 100 parts by mass, which was used as it was.

Comparative Example 14

Pegnol ST-9 (which is a trade name, manufactured by TOHO Chemical Industry Co., LTD.: containing 100% polyoxyethylene alkyl (C12 to 14) ether and having a polyoxyethylene polymerization degree of 9): 100 parts by mass, which was used as it was.

Comparative Example 15

Mixpower® (which is a trade name, manufactured by Syngenta: 40% polyoxyethylene octylphenyl ether and 40% polyoxyethylene alkyl ether): 100 parts by mass, which was used as it was.

Test Example 1

Adhesion Test of Fluorescent Pigment (Cabbage)

As for the compositions obtained in the above Examples 1 to 10 and Comparative Examples 1 to 12, adhesion (adhesion uniformity) to crops was observed by the following test method. The results are shown in Table 1-1 and the evaluation criteria are shown in Table 1-2.

(1) Preparation Method of "Fluorescent Pigment+Adjuvant Composition"

To 10 L of tap water, 10 ml (1000 times dilution) of Sinloihi® SW-11 (which is a trade name, manufactured by SINLOIHI Co. Ltd.: fluorescent pigment, water-soluble) having luminescence intensity at 365 nm and light fastness and a predetermined amount of a sample agent were added, and the mixture was sufficiently stirred to prepare a spray aqueous solution.

(2) Measuring Apparatus for Spray Particle Drift, Particle Size and Adhesion (Owned by National Agriculture and Food Research Organization, Bio-Oriented Technology Research Advancement Institution, Crop Production Machinery and System Department, Crop Tending Machinery Laboratory)

Inside size of wind tunnel in spraying equipment: 4 m entire length, 2 m width, 2 m height Nozzle height: about 45 cm from the top of the target crops Nozzle used:

Customary nozzle: New wide-angle spray nozzle plate (which is a trade name, manufactured by YAMAHO Industry Co., Ltd.: the total volume ratio of the particles having a size of 100 μm or less is 60% or more (1.0 to 2.0 MPa))

Drift-reducing nozzle: Kirinashi ES Tip (which is a trade name, manufactured by YAMAHO Industry Co., Ltd.: the total volume ratio of the particles having a size of 100 μm or less is 10% or less (1.0 to 2.0 MPa))

Travel velocity: 0.88 m/sec. (customary nozzle), 0.56 m/sec. (drift-reducing nozzle)

Spray pressure: 1.5 MPa

Sprayed liquid amount: equivalent to 100 L/10 are (effective spray width per nozzle: 0.3 m)

(3) Spray Conditions

In the center of the nozzle travel area, expanded polystyrene having a size of 1.5 m×1.5 m square was placed and then cabbage about 2 months after seeding (in states 12 to 15) was placed in the center, and artificial flowers were placed in the surrounding eight positions 30 cm away.

(4) Spraying Method of Fluorescent Pigment

The diluted liquid of "the fluorescence pigment+a sample adjuvant composition" prepared in the above (1) was sprayed under the conditions (2) and (3).

(5) Examination Method for Adhesion State of Fluorescence Pigment

After the diluted liquid of "the fluorescence pigment+a sample adjuvant composition" was sprayed and then the sprayed liquid was dried, ultraviolet rays of 365 nm were irradiated in the dark using an ultraviolet ray lamp and the irradiated state was photographed with a digital camera (body: Canon EOS kiss Digital X (which is a trade name, manufactured by Canon Inc.), lens: EF-S18-55 mm F3.5-5.6 II USM (which is a trade name, manufactured by Canon Inc.)

TABLE 1-1

| Sample adjuvant composition | Addition amount per 10 L of tap water (surfactant component concentration in sample agent in spray aqueous solution) | Photograph result (evaluation of photograph by visual observation) Drift-reducing nozzle | Photograph result (evaluation of photograph by visual observation) Customary nozzle |
|---|---|---|---|
| Example 1 | 3.3 ml (235 ppm) | +++ | +++++ |
| Example 2 | 3.3 ml (257 ppm) | +++ | +++++ |
| Example 3 | 3.3 ml (244 ppm) | +++ | +++++ |
| Example 4 | 3.3 ml (257 ppm) | ++ to +++ | ++++ |
| Example 5 | 3.3 ml (239 ppm) | ++ to +++ | ++++ |
| Example 6 | 3.3 ml (224 ppm) | +++ | +++++ |
| Example 7 | 3.3 ml (235 ppm) | ++ to +++ | ++++ |
| Example 8 | 3.3 ml (224 ppm) | ++ to +++ | ++++ |
| Example 9 | 3.3 ml (224 ppm) | ++ to +++ | ++++ |
| Example 10 | 3.3 ml (254 ppm) | ++ to +++ | ++++ |
| Comparative Example 1 | 3.3 ml (106 ppm) | + | +++ |
| Comparative Example 2 | 3.3 ml (99 ppm) | + | +++ |
| Comparative Example 3 | 10 ml (620 ppm) | + | |
| Comparative Example 4 | 10 ml (500 ppm) | + to ++ | +++ |
| Comparative Example 5 | 3.3 ml (231 ppm) | + | |
| Comparative Example 6 | 3.3 ml (330 ppm) | + | |
| Comparative Example 7 | 3.3 ml (264 ppm) | + | ++ |
| Comparative Example 8 | 3.3 ml (129 ppm) | + | |
| Comparative Example 9 | 3.3 ml (99 ppm) | + | |
| Comparative Example 10 | 3.3 ml (102 ppm) | + | |
| Comparative Example 11 | 3.3 ml (132 ppm) | + | +++ |
| Comparative Example 12 | 3.3 ml (41 ppm) | + | ++ |

Criteria of adhesion evaluation: Judged by visual observation of photo images with the digital camera.

TABLE 1-2

| Evaluation criteria | Old leaf/horizontal | Middle leaf | Young leaf/perpendicular |
|---|---|---|---|
| + | Partially adhered | Partially adhered | Hardly adhered |
| ++ | Adhered to about half or more | Partially adhered | Hardly adhered |
| +++ | Nearly adhered to the whole | Nearly adhered whole | Partially adhered |
| ++++ | Uniformly adhered to the whole | Nearly adhered to the whole | Adhered to about half or more |
| +++++ | Uniformly adhered to the whole | Uniformly adhered to the whole | Uniformly adhered to the whole |

From Table 1-1, it is found that Examples 1 to 10 of the present invention has extremely good adhesion properties compared with Comparative Examples 1 to 12. In particular, the difference is significant in the drift-reducing nozzle of a large spray particle size which is regarded to lead to poor adhesion properties. For example, in Comparative Examples, only partial adhesion to old leaves and middle leaves which are easily adhered were observed, and there were almost no adhesion to young leaves and vertical leaves, and most part were stayed on the stems. On the other hand, adhesion properties in Examples were improved, and adhesion not only to old leaves and middle leaves but also to young leaves and vertical leaves to which adhesion is poor were observed. In addition, with respect to customary nozzle, uniform adhesion to the whole were observed in Examples 1 to 10, while the adhesion state in Comparative Examples particularly to young leaves were not good. In this connection, Examples 4, 5, 7, 8 and 9 showed better results than Comparative Examples, but the adhesion properties thereof slightly deteriorated compared with the other Examples. It is estimated to be affected by the low polymerization degree of polyoxyethylene in polyoxyethylene alkyl ether.

Test Example 2

Adhesion Test of Fluorescent Pigment (Long Green Onion)

The adhesion state (adhesion uniformity) of the compositions obtained in the above Examples 1 to 6 and Comparative Examples 1, 2, 8, and 13 to 15 to crops was observed by the following test method. The results are shown in Table 2-1 and the evaluation criteria are shown in Table 2-2.

(1) Preparation Method of Fluorescent Pigment+Adjuvant Composition

To 10 L of tap water, 10 ml (1000 times dilution) of Sinloihi® SW-11 (which is a trade name, manufactured by SIN-LOIHI Co. Ltd.: fluorescent pigment and water-soluble) having luminescence intensity at 365 nm and light fastness and a predetermined amount of a sample agent were added, and the mixture was sufficiently stirred to prepare a spray aqueous solution.

(2) Measuring Apparatus for Spray Particle Drift, Particle Size and Adhesion (Owned by National Agriculture and Food Research Organization, Bio-Oriented Technology Research Advancement Institution, Crop Production Machinery and System Department, Crop Tending Machinery Laboratory)

Inside size of wind tunnel in spraying equipment: 4 m entire length, 2 m width, 2 m height Nozzle height: about 45 cm from the top of the target crops Nozzle used:

Drift-reducing nozzle: Kirinashi ES Tip (which is a trade name, manufactured by YAMAHO Industry Co., Ltd.: the total volume ratio of the particles having a size of 100 μm or less is 10% or less (1.0 to 2.0 MPa))

Travel velocity: 0.56 m/sec. (drift-reducing nozzle)

Spray pressure: 1.5 MPa

Sprayed liquid amount: equivalent to 200 L/10 are (effective spray width per nozzle: 0.3 m)

(3) Spray Conditions

In the center of the nozzle travel area, expanded polystyrene having a size of 1.5 m×1.5 m square was placed, and then in its center Fukaya Negi (long green onion) (height: about 80 cm) before harvesting were placed at intervals of about 15 cm in the horizontal travel direction of a boom sprayer so that they were not crossover.

(4) Spraying Method of Fluorescent Pigment

A diluted liquid of "the fluorescence pigment+a sample adjuvant composition" prepared in the above (1) was sprayed under the conditions (2) and (3).

(5) Examination Method for Adhesion State of Fluorescence Pigment

After the diluted liquid of "the fluorescence pigment+a sample adjuvant composition" was sprayed and then the sprayed liquid was dried, ultraviolet rays of 365 nm were irradiated in the dark using an ultraviolet ray lamp and the irradiated state was photographed with a digital camera (body: Canon EOS kiss Digital X (which is a trade name, manufactured by Canon Inc.), lens: EF-S18-55 mm F3.5-5.6 II USM (which is a trade name, manufactured by Canon Inc.)

TABLE 2-1

| Sample adjuvant composition | Addition amount per 10 L of tap water (surfactant component concentration in sample agent in spray aqueous solution) | Photograph result (evaluation of photograph by visual observation) Drift-reducing nozzle |
|---|---|---|
| Example 1 | 3.3 ml (235 ppm) | +++ to ++++ |
| Example 2 | 3.3 ml (257 ppm) | +++ to ++++ |
| Example 3 | 3.3 ml (244 ppm) | +++ to ++++ |
| Example 4 | 3.3 ml (257 ppm) | +++ |
| Example 5 | 3.3 ml (239 ppm) | +++ |
| Example 6 | 3.3 ml (224 ppm) | +++ to ++++ |
| Comparative Example 1 | 3.3 ml (106 ppm) | + |
| Comparative Example 2 | 3.3 ml (99 ppm) | + |
| Comparative Example 8 | 3.3 ml (129 ppm) | ++ to +++ |
| Comparative Example 13 | 3.3 ml (297 ppm) | + to ++ |
| Comparative Example 14 | 3.3 ml (330 ppm) | + |
| Comparative Example 15 | 3.3 ml (264 ppm) | + |

Criteria of adhesion evaluation: Judged by visual observation of photo images with the digital camera.

TABLE 2-2

| Evaluation criteria | Adhesion to long green onion surface |
|---|---|
| + | Partially adhered |
| ++ | Adhered to about half or more |
| +++ | Nearly adhered to the whole |
| ++++ | Uniformly adhered to the whole |

From Table 2-1, it can be confirmed that Examples 1 to 6 of the present invention have good adhesion properties compared with Comparative Examples 1, 2, 8, 13 to 15. Although the long green onion has a vertically long plant height and it is empirically known that adhesion properties of agrochemicals to the surface thereof are poor, and thus it is a crop to which adhesion is poor, Examples show better adhesion properties thereto than Comparative Example 15 which is a combination of polyoxyethylene alkyl ether and polyoxyethylene octylphenyl ether, Comparative Example 13 containing 90% by mass of sodium dialkylsulfosuccinate and Comparative Example 14 containing 100% by mass of polyoxyethylene alkyl ether, and thus it was confirmed that adhesion properties were improved by a mixed product of polyoxyethylene alkyl ether and sodium dialkylsulfosuccinate. In addition, Comparative Example 8, in which the total content of a mixed product of polyoxyethylene alkyl ether and sodium dialkylsulfosuccinate is 40% by mass, shows worse results in adhesion properties than Examples. For that reason, it can be said that the concentration that the total content of a surfactant component is more than at least 40% by mass is preferable for improvement of stable adhesion properties.

Test Example 3

Evaluation Test of Wetting Properties of Crop Surface (Cabbage)

The compositions obtained in the above Examples 1, 2, 3, 6, 7 and 10 and Comparative Examples 1, 3, 8, 9, 10, 13 and 14 were evaluated for wetting properties of crop surface by the following test method. The results are shown in Table 3-1 and the evaluation criteria are shown Table 3-2.

(1) Preparation Method of Spray Aqueous Solution

To 10 L of tap water, a predetermined amount of a sample agent was added, and the mixture was sufficiently stirred to prepare a spray aqueous solution.

(2) Spraying Method

Cabbage (in 12 to 15 leaves stage) in about 2 months after seeding was placed on the ground; using a spray gun named Anest Iwata PS95 (manufactured by Anest Iwata Corporation), the liquid was sprayed at a height of about 45 cm from the crop, a spray pressure of 0.24 MPa and a rate of 400 ml/1 m² (equivalent to 400 L/10 a) (total volume ratio of the particles having a size of 100 μm or less is 80%); and the adhesion state of the water droplets was evaluated by visual observation.

TABLE 3-1

| Sample adjuvant composition | Addition amount per 10 L of tap water (surfactant component concentration in sample agent in spray aqueous solution) | Evaluation by visual observation |
|---|---|---|
| Example 1 | 3.3 ml (235 ppm) | +++++ |
| Example 2 | 3.3 ml (257 ppm) | +++++ |
| Example 3 | 3.3 ml (244 ppm) | +++++ |
| Example 6 | 3.3 ml (224 ppm) | +++++ |
| Example 7 | 3.3 ml (235 ppm) | ++++ |
| Example 10 | 3.3 ml (254 ppm) | +++++ |
| Comparative Example 1 | 3.3 ml (106 ppm) | ++ |
| Comparative Example 3 | 10 ml (620 ppm) | ++ to +++ |
| Comparative Example 8 | 3.3 ml (129 ppm) | ++ to +++ |
| Comparative Example 9 | 3.3 ml (99 ppm) | ++ |
| Comparative Example 10 | 3.3 ml (102 ppm) | ++ |
| Comparative Example 13 | 3.3 ml (297 ppm) | ++ to +++ |
| Comparative Example 14 | 3.3 ml (330 ppm) | ++ to +++ |

Evaluation Criteria of Visual Observation:

TABLE 3-2

| Evaluation criteria | Old leaf/horizontal | Middle leaf | Young leaf/ perpendicular |
|---|---|---|---|
| + | Partially adhered | Partially adhered | Hardly adhered |
| ++ | Adhered to about half or more | Partially adhered | Hardly adhered |
| +++ | Nearly adhered to the whole | Nearly adhered to the whole | Partially adhered |
| ++++ | Uniformly adhered to the whole | Nearly adhered to the whole | Adhered to about half or more |
| +++++ | Uniformly adhered to the whole | Uniformly adhered to the whole | Uniformly adhered to the whole |

Judging from Table 3-1, the wetting properties of the surface of the cabbage crop in Examples 1, 2, 3, 6, 7 and 10 of the present invention are improved compared with Comparative Examples 1, 3, 8, 9, 10, 13 and 14. In Examples, wetting properties were particularly observed not only in old leaves and middle leaves but also in young leaves and perpendicular leaves to which adhesion is poor. In Comparative Examples 13 and 14, the wetting properties of a liquid containing 90% sodium dialkylsulfosuccinate and a liquid containing 100% polyoxyethylene alkyl ether were evaluated. Compared with these, the wetting properties of Examples of a mixed product of polyoxyethylene alkyl ether and sodium dialkylsulfosuccinate were clearly improved. In addition, Comparative Example 8 has insufficient wetting properties even if it is a mixed product of polyoxyethylene alkyl ether and sodium dialkylsulfosuccinate because the total content of the both is 40% by mass, and thus a higher total concentration in a spray aqueous solution to some extent imparts excellent wetting properties (adhesion properties of agent) even though it is a mixed product of polyoxyethylene alkyl ether and sodium dialkylsulfosuccinate, whereby it was confirmed that the total content of the both in an adjuvant composition is preferably 40% or more for wetting properties (adhesion properties of agent) when the dilution factor is about 3000 times.

Test Example 4

Measurement Test for Adhesion Amount of Agrochemical Active Ingredient to Cabbage Leaves The adhesion state of the compositions obtained in the above Example 2 and Comparative Example 1 to cabbage as a target crop was examined by the following test method.

(1) Sample Agrochemical Formulation

Kotetsu Flowable (which is a trade name, manufactured by Nippon Soda Co., Ltd.: the active ingredient is 10% Chlorfenapyr)

(2) Dilution Factor and Spray Concentration of Sample Agrochemical Formulation

TABLE 4-1

| Sample agrochemical formulation | Addition amount per 10 L | Concentration of agrochemical component in diluted liquid |
|---|---|---|
| Kotetsu Flowable | 5 ml | 50 ppm |

(3) Dilution Factor and Spray Concentration of Sample Adjuvant Composition

TABLE 4-2

| Sample adjuvant composition | Addition amount per 10 L | Concentration of surfactant in diluted liquid |
|---|---|---|
| Example 2 | 3.3 ml | 257 pm |
| Comparative Example 1 | 3.3 ml | 106 ppm |

(4) Preparation Method of Agrochemical Spray Aqueous Solution of Agrochemical Formulation+Adjuvant Composition Into a 10 L volume bucket, 10 L of tap water was put, and then each adjuvant composition of Example and Comparative Example in (3) was added at a predetermined concentration and the mixture was stirred followed by addition of the agrochemical formulation of (2) at a predetermined concentration to prepare an agrochemical spray aqueous solution.

(5) Spreader and Spray Condition

Spreader used: Power sprayer GS60M (which is a trade name, manufactured by Maruyama MFG. Co., Inc.)

Nozzle height: about 45 cm from the top of the target crop

Nozzle used:

Customary nozzle: New wide-angle spray nozzle plate (which is a trade name, manufactured by YAMAHO Industry Co., Ltd.: the total volume ratio of the particles having a size of 100 μm or less is 60% or more (spray pressure: 1.0 to 2.0 MPa)); Drift-reducing nozzle: Kirinashi. ES Tip (which is a trade name, manufactured by YAMAHO Industry Co., Ltd.: the total volume ratio of the particles having a size of 100 μm or less is 10% or less (spray pressure: 1.0 to 2.0 MPa))

Spray pressure: 1.5 MPa (pressure on the supply port)

Spray velocity: 0.88 m/sec. (customary nozzle), 0.56 m/sec. (drift-reducing nozzle)

Spray rate: equivalent of 100 L/10 are (effective spray width per nozzle: 0.3 m)

(6) Spraying Method of Agrochemical Spray Aqueous Solution

In nozzle travel area, three heads of cabbage 2 months after seeding (in leaf stages 12 to 15) were placed at intervals of 30 cm and the agrochemical spray aqueous solution prepared in (4) was sprayed under the conditions of (5).

(7) Sampling Method of Cabbage Leaf for Analysis

Cabbage leaves 12 hours after spraying were categorized according to the following Table 4-3 and collected.

TABLE 4-3

| Sample collecting position | Angle from ground | |
|---|---|---|
| Upper side | 60 to 90° | Young and angled leaves are hardly adhered. |
| Mid side | 30 to 60° | |
| Lower side | 0 to 30° | There are a lot of old leaves and adhesion is easy. |

(8) Analysis Condition (HPLC)

Column: Inertsil ODS-3 (which is a trade name, manufactured by GL Sciences Inc.: φ 4.5 μm L=150 mm)
Column temperature: 40° C.
Mobile phase: acetonitrile/water=70/30 (v/v)
Flow rate: 1.5 mL/min
Wavelength: 254 nm
Retention time: Chlorfenapyr=6.73 min
Injection volume: 20 uL (9) Analytical Operation Cabbage leaves after spraying were collected at the upper, mid, and lower sides of the cabbage and put into a 200 ml conical flask, and then 20 ml of acetonitrile was added and the mixture was shaken by hand for 1 to 2 minutes to extract the agrochemical active ingredient adhered to the surface. The extract was injected into HPLC as it was, and the adhesion amount of the agrochemical active ingredient per 1 g of cabbage leaf was measured. The results are shown in Table 4-4. In this connection, "customary" stands for customary nozzle and drift reduction stands for drift-reducing nozzle, in the column of nozzle type in Table 4-4. In addition, this is the same in the other Tables.

Adhesion Amount of Chlorfenapyr to Cabbage Leaf

TABLE 4-4

| Nozzle type | Sample agrochemical formulation | Sample adjuvant composition | Analysis position | Adhered amount μg/g | Average adhered amount μg/g |
|---|---|---|---|---|---|
| Customary | Kotetsu | Comparative Example 1 | Upper side | 2.18 | 2.19 |
| Customary | Kotetsu | Comparative Example 1 | Mid side | 1.99 | |
| Customary | Kotetsu | Comparative Example 1 | Lower side | 2.40 | |
| Drift reduction | Kotetsu | Comparative Example 1 | Upper side | 0.10 | 0.55 |
| Drift reduction | Kotetsu | Comparative Example 1 | Mid side | 0.77 | |
| Drift reduction | Kotetsu | Comparative Example 1 | Lower side | 0.78 | |
| Drift reduction | Kotetsu | Example 2 | Upper side | 2.39 | 2.52 |
| Drift reduction | Kotetsu | Example 2 | Mid side | 3.86 | |
| Drift reduction | Kotetsu | Example 2 | Lower side | 1.32 | |

Judging from Table 4-4, in the case of using the composition of Example 2, the adhesion amount of the agrochemical is significantly increased on any of upper side, mid side and lower side with a drift-reducing nozzle causing poor adhesion properties of agrochemical active ingredients, compared with the case of using the composition of Comparative Example 1; and the agrochemical spray aqueous solution using the composition of Example 2 shows good adhesion properties. In particular, the adhesion properties to the leaves in the mid side position and the upper side position are particularly good. In addition, the average adhesion amount of the agrochemical active ingredient in the case of spraying the agrochemical spray aqueous solution using the composition of Example 2 with a drift-reducing nozzle is more than that in the case of spraying the agrochemical spray aqueous solution using the compound of Comparative Example 1 with a customary nozzle, and thus it is found that by using the compound of Example 2, agrochemical effect with a drift-reducing nozzle is expected as well as or more than that with a customary nozzle.

Test Example 5

Insecticide Test of Plutella xylostella

Insecticide test of Plutella xylostella was carried out on the compositions obtained in the above Example 2 and Comparative Example 1 by the following test method.

(1) Sample Agrochemical Formulation and Spray Concentration

Kotetsu Flowable (which is a trade name, Nippon Soda Co., Ltd.: the active ingredient is 10% Chlorfenapyr)
Spray concentration: 50 ppm (2) Dilution Factor and Spray Concentration of Sample Adjuvant Composition

TABLE 5-1

| Sample adjuvant composition | Addition amount per 10 L | Concentration of surfactant component in diluted liquid |
|---|---|---|
| Example 2 | 3.3 ml | 257 ppm |
| Comparative Example 1 | 3.3 ml | 106 ppm |

(3) Preparation Method of Agrochemical Spray Aqueous Solution of "Agrochemical Formulation+Adjuvant Composition"

Into a 10 L volume bucket, 10 L of tap water was put, and then a predetermined amount of each adjuvant composition of Example 2 and Comparative Example 1 in (2) was added and the mixture was stirred sufficiently, followed by addition of a sample agrochemical formulation so that the predetermined concentration was made, to prepare an agrochemical spray aqueous solution.

(4) Spreader and Spray Condition

Spreader used: motor power sprayer GS60M (which is a trade name, manufactured by Maruyama MFG. Co., Inc.)

Nozzle height: about 45 cm from the top of the target crop

Nozzle used: customary nozzle: New wide-angle spray nozzle plate (which is a trade name, manufactured by YAMAHO Industry Co., Ltd.: the total volume ratio of the particles having a size of 100 μm or less is 60% or more (spray pressure: 1.0 to 2.0 MPa))

Drift-reducing nozzle: Kirinashi ES Tip (which is a trade name, manufactured by YAMAHO Industry Co., Ltd.: the total volume ratio of the particles having a size of 100 μm or less is 10% or less (spray pressure: 1.0 to 2.0 MPa))

Spray pressure: 1.5 MPa (pressure on the supply port)

Spray velocity: 0.88 m/sec. (customary nozzle), 0.56 m/sec. (drift-reducing nozzle)

Spray rate: equivalent to 200 L/10 are (effective spray width per nozzle: 0.3 m)

(5) Spraying Method of Agrochemical Spray Aqueous Solution

In the nozzle travel area, 5 heads of cabbage 2 months after seeding (in leaf states 12 to 15) were placed at intervals of 30 cm and the prepared agrochemical spray aqueous solution was sprayed under the conditions of (4).

(6) Insecticide Test

After completion of the spraying, 7 hatchlings of *Plutella xylostella* per head were inoculated into the air-dried cabbage heads (4 hatchlings into the third youngest leaf and 3 hatchlings into the fifth youngest leaf). Eight days later, the numbers of the surviving larvaes were examined and the mortality was calculated. The results are indicated in Table 5-2.

TABLE 5-2

| Nozzle type | Sample adjuvant composition | Number of larva of *Plutella xylostella* (total number in the 5 heads) | Mortality |
|---|---|---|---|
| Customary | Comparative Example 1 | 9 | 57.1 |
| Customary | Example 2 | 0 | 100 |
| Drift reduction | Comparative Example 1 | 14 | 33.3 |
| Drift reduction | Example 2 | 3 | 85.7 |
|  | Non-treated area | 21 | 0 |

Judging from the results in Table 5, even though any of a customary nozzle and a drift-reducing nozzle is used, the addition of the sample adjuvant composition in Example 2 of the present invention shows a higher mortality than the addition of the sample adjuvant composition in Comparative Example 1. From this, it is clear that the adjuvant composition of the present invention makes agrochemical efficacy stable.

The invention claimed is:

1. An adjuvant composition wherein the adjuvant composition contains the following (A) component and (B) component in the following range:
   (A) Sodium bis(2-ethylhexyl)sulfosuccinate and polyoxyethylene alkyl C11 to C15 ether as surfactant components, the total content of the both being 45 to 85% by mass;
   (B) A component for pour-point depressant, wherein said component is a C2 to C4 alkylene glycol and water, in an amount of 5 to 40% by mass; relative to the whole adjuvant composition, and the total content of (A) component and (B) component relative to the whole adjuvant composition is more than 50% by mass.

2. The adjuvant composition according to claim 1, wherein the mixture ratio of the sodium bis(2-ethylhexyl)sulfosuccinate and the polyoxyethylene alkyl ether is 4:1 to 1:5.

3. The adjuvant composition according to any one of claim 1 or 2, wherein the alkyl chain of polyoxyethylene alkyl ether is in the range of C12 to C14.

4. The adjuvant composition according to claim 1, wherein the glycol is propylene glycol.

5. The adjuvant composition according to any one of claim 1 or 2, wherein said polyoxyethylene alkyl ether comprises polyoxyethylene alkyl (C12 to C14) ether.

6. The adjuvant composition according to any one of claim 1 or 2, wherein the adjuvant composition is for drift-reducing spray.

7. An agrochemical spray aqueous solution wherein the adjuvant composition according to any one of claim 1 or 2 is added to a diluted liquid containing an agrochemical active ingredient.

8. The agrochemical spray aqueous solution according to claim 7, wherein the amount of the adjuvant composition to be added is 0.5 to 10 ml per 10 L of the diluted liquid.

9. The agrochemical spray aqueous solution according to claim 7, where the concentration of the surfactant component in the agrochemical spray aqueous solution is 50 to 1000 ppm.

10. A method for spraying an agrochemical, wherein the agrochemical spray aqueous solution according to claim 7 is sprayed using a spreader.

11. The method for spraying an agrochemical according to claim 10, wherein the total volume ratio of the spray particles having a particle size of 100 μm or less is 40% or less when the agrochemical spray aqueous solution is sprayed.

12. The method for spraying an agrochemical according to claim 11, wherein a nozzle for spraying is a nozzle for drift-reducing spray where the total volume ratio of the spray particles having a particle size of 100 μm or less is 40% or less when the agrochemical spray aqueous solution is sprayed.

13. A method for controlling a pest insect, fungus and/or weed, wherein the agrochemical spray aqueous solution of claim 7 is sprayed using a spray nozzle where the volume median diameter of the spray particles is 100 μm or more and the total volume ratio of the spray particles having a particle size of 100 μm or less is 40% or less.

14. An adjuvant composition, wherein:
   (A) Sodium bis(2-ethylhexyl)sulfosuccinate and polyoxyethylene C11 to C15 alkyl ether (the polymerization degree of the polyoxyethylene is 3 to 15) are contained as surfactant components, the total content of the both is 45 to 85% by mass relative to the whole adjuvant composition, the content of said polyoxyethylene C11 to C15 alkyl ether is 20 to 70% by mass, and the mass ratio of sodium bis(2-ethylhexyl)sulfosuccinate:polyoxyethylene C11 to C15 alkyl ether is in the range of 4:1 to 1:5;
   (B) C2 to C4 alkylene glycol water is contained in an amount of 10 to 35% by mass, as a component for pour-point depressant;
   and the rest is an optional component other than the above.

15. The adjuvant composition according to claim 14, wherein the polymerization degree of the polyoxyethylene in the polyoxyethylene C11 to C15 alkyl ether is 7 to 12, and the C2 to C4 alkylene glycol is propylene glycol.

16. The adjuvant composition according to claim 14 or 15, wherein the content of the C2 to C4 alkylene glycol or the propylene glycol is 5 to 25% by mass.

17. The adjuvant composition according to claim 14 or 15, wherein C2 to C4 alkylene glycol and water are contained as components for pour-point depressant, the total content of the both is 5 to 35% by mass relative to the whole adjuvant composition, and the ratio of C2 to C4 alkylene glycol:water is 1:1 to 2:1.

18. The agrochemical spray aqueous solution wherein agrochemical active ingredient, sodium bis(2-ethylhexyl)sulfosuccinate, polyoxyethylene alkyl ether, C2 to C4 alkylene glycol and water are contained, the concentration of the agrochemical active ingredient is 5 to 1000 ppm, the total concentration of sodium bis(2-ethylhexyl)sulfosuccinate and polyoxyethylene alkyl ether as surfactant components (A) is 150 to 300 ppm relative to the whole spray aqueous solution, and the concentration of the C2 to C4 alkylene glycol is 20 to 100 ppm relative to the whole spray aqueous solution.

\* \* \* \* \*